US006473717B1

(12) United States Patent
Claussen et al.

(10) Patent No.: US 6,473,717 B1
(45) Date of Patent: Oct. 29, 2002

(54) METHOD AND APPARATUS FOR EVALUATING A MOVEMENT PATTERN

(76) Inventors: Claus-Frenz Claussen, Kurhausstrasse 12, D-97688 Bad Kissingen (DE); Svetlozar Haralanov, 74 B Sveti Georgy Sofiisky Street, BG-1606 Sofia (BG)

( * ) Notice: Subject to any disclaimer, the term of this patent is extended or adjusted under 35 U.S.C. 154(b) by 0 days.

(21) Appl. No.: 09/657,075
(22) Filed: Sep. 7, 2000

Related U.S. Application Data

(63) Continuation of application No. PCT/EP98/01341, filed on Mar. 7, 1998.

(51) Int. Cl.$^7$ ................................................. G06G 7/48
(52) U.S. Cl. .......................... 702/153; 702/94; 702/95; 702/150; 702/151; 702/152
(58) Field of Search ........................... 702/94, 95, 150, 702/151, 152, 153; 348/121, 135, 136; 345/473, 474, 475, 952, 953, 959; 356/620; 600/595; 382/103, 151, 291; 250/227.29; 364/559; 73/65.01

(56) References Cited

U.S. PATENT DOCUMENTS

| | | | |
|---|---|---|---|
| 4,631,676 A | | 12/1986 | Pugh |
| 4,813,436 A | * | 3/1989 | Au ............................ 128/779 |
| 5,086,404 A | * | 2/1992 | Claussen ................... 364/559 |
| 5,203,346 A | * | 4/1993 | Fuhr et al. .................. 128/781 |
| 5,562,104 A | * | 10/1996 | Hochberg et al. .......... 128/782 |
| 5,823,958 A | * | 10/1998 | Truppe ....................... 600/426 |
| 5,891,060 A | * | 4/1999 | McGregor et al. .......... 600/595 |
| 5,954,674 A | * | 9/1999 | Fuhr ........................... 600/594 |

(List continued on next page.)

FOREIGN PATENT DOCUMENTS

DE    38 29 885 A1    3/1990

OTHER PUBLICATIONS

International Publication No. WO 91/15148 (Winters et al.), dated Oct. 17, 1991.
"Three–dimensional measurement system for functional arm motion study" (Safaee–Rad et al.), Medical and Biological Engineering & Computing, Nov. 1990, pp. 569–573.
"The reliability of postural sway measures using the 3space tracker" (Carrera et al.), Clinical Biomechanics, vol. 11, No. 6, Sep. 1, 1996, pp. 361–363.

Primary Examiner—Marc S. Hoff
Assistant Examiner—Carol S Tsai
(74) Attorney, Agent, or Firm—Laurence A. Greenberg; Werner H. Stemer; Ralph E. Locher (57) ABSTRACT

A method for evaluating a head and trunk movement pattern of a subject includes configuring a plurality of markers to move together with the body of a subject. For each of the plurality of markers, a locus curve in three-dimensional space is detected as a function of time and the locus curve is stored as a data field of a measured data record that is common to the plurality of markers. The movement pattern of the body of the subject is characterized using characteristic variables derived from the measured data record. Reference variables are derived from a stored plurality of reference data records. Each of the characteristic variables is compared with the reference variables derived from the stored reference data records. Each of the characteristic variables is derived from a projection of the locus curve of at least one of the markers onto one of the three datum planes of a Cartesian coordinate system. It is thus possible to interpret the evaluated kinetic pattern and use this information to provide a diagnostic of the basic clinical picture, especially following psychic, psychosomatic and/or neurological disorders.

17 Claims, 3 Drawing Sheets

U.S. PATENT DOCUMENTS

| | | | | |
|---|---|---|---|---|
| 5,961,923 A | * | 10/1999 | Nova et al. | 422/68.1 |
| 5,963,891 A | * | 10/1999 | Walker et al. | 702/150 |
| 5,991,701 A | * | 11/1999 | Triano | 702/150 |
| 6,056,703 A | * | 5/2000 | Sandler et al. | 600/593 |
| 6,079,862 A | * | 6/2000 | Kawashima et al. | 364/167.6 |
| 6,124,838 A | * | 9/2000 | Lasko-Harvill et al. | 345/8 |
| 6,213,958 B1 | * | 4/2001 | Winder | 600/586 |
| 6,223,064 B1 | * | 4/2001 | Lynn et al. | 600/324 |

* cited by examiner

METHOD AND APPARATUS FOR EVALUATING A MOVEMENT PATTERN

CROSS-REFERENCE TO RELATED APPLICATION

This is a continuation of copending international application PCT/EP98/01341, filed Mar. 7, 1998, which designated the United States.

BACKGROUND OF THE INVENTION

Field of the Invention

The invention relates to a method for evaluating a movement pattern that is recorded using a number of markers moving together with the body of a subject. It relates further to a corresponding apparatus for carrying out the method. In this context, movement pattern is understood to mean the pattern of the head and trunk movement (cranio-corpo-gram).

Balance dysfunctions occur as a main or consequential phenomenon of a multiplicity of pathological findings. In the first instance, these are constitutional phenomena, such as vertigo, or damage caused during an accident, e.g. whiplash. In the second instance, numerous clinical pictures are linked to reversible or irreversible balance control disorders, also including psychosomatic illnesses, such as schizophrenia, dementia, depression and Parkinson's syndrome. Particularly when a person is standing up, keeping one's balance requires a highly complicated control mechanism that involves not only the organ of balance (vestibular apparatus) situated in the inner ear but also, in particular, the eyes and ears as well as touch receptors and various regions of the brain. The so-called "cranio-corpo-graphy" method of examination used for diagnosis purposes leads to the realization that disorders in various regions of the organs involved in balance control produce a particular characteristic movement pattern in a subject to be examined. By observing the movement pattern, cranio-corpo-graphy can be used to locate the disorder empirically within the balance control system. This in turn allows conclusions to be drawn about the illness causing the balance dysfunction.

On the basis of the device disclosed in the document "Forschungsbericht Cranio-Corpo-Graphie (CCG) [Cranio-corpo-graphy (CCG) Research Report]", ISBN 3-88383-126-3 (June 1986), which appeared in the documentary series of the Hauptverband der gewerblichen Berufsgenossenschaften e.V. [Main association of the registered organization of professional business associations], the head and trunk movement of a subject is made visible using markers in the form of incandescent lamps. A respective lamp is positioned on each of the subject's two shoulders, one is positioned above his/her forehead and one is positioned at the back of his/her head. The movement of each marker in the horizontal plane is recorded photographically by a camera configured above the subject under continuous exposure as a luminous trace in a so-called cranio-corpo-gram. The luminous traces are evaluated manually on the photograph after the experiment has been carried out.

However, manual evaluation of the recordings, which is done either by measuring the geometry of the luminous traces or by associatively linking the complex movement pattern to comparison patterns, termed "graphical element", is associated with a considerable time requirement. Furthermore, a fundamental disadvantage is that some of the information produced in the experiment is lost during photographic recording of the marker movement. Thus, the photograph shows only the horizontal components of the marker movement. It is thus not possible to make any statements about vertical movements and the absolute height of a marker in space. Complex calibration of the photograph is therefore necessary in order to be able to compare cranio-corpo-grams for subjects of different heights. Since the luminous traces of all the markers are contained in a single photograph, there is often masking due to the luminous traces overlapping, which makes it more difficult, or even impossible, to characterize an individual luminous trace. Information is also lost in the blind angle, which is situated directly below the camera and in which the camera projects into the path of rays running between the mirror and a marker.

DE 38 29 885 C2 discloses a device in which, instead of a camera, a configuration of photoelectric cells positioned above the subject is used for recording the luminous traces. This configuration eliminates the blind angle. In this case, the luminous traces are analyzed using a digital computer for calculating the movement deviations relevant to cranio-corpo-graphy. However, this does not provide for evaluation in terms of interpreting recorded movement patterns.

SUMMARY OF THE INVENTION

It is accordingly an object of the invention to provide a method and a device for evaluating movement patterns recorded using a number of markers moving together with the body of a subject, which overcomes the hereinafore-mentioned disadvantages of the heretofore-known methods and devices of this general type in such a way that the movement pattern can be evaluated while maintaining a particularly high information density and without taking up a lot of time.

With the foregoing and other objects in view there is provided, in accordance with the invention, a method for evaluating a head and trunk movement pattern of a subject that includes configuring a plurality of markers to move together with the body of a subject. For each of the plurality of markers, a locus curve in three-dimensional space is detected as a function of time and the locus curve is stored as a data field of a measured data record that is common to the plurality of markers. The movement pattern of the body of the subject is characterized using characteristic variables derived from the measured data record. Reference variables are derived from a stored plurality of reference data records. Each of the characteristic variables is compared with the reference variables derived from the stored reference data records. Each of the characteristic variables is derived from a projection the locus curve of at least one of the plurality of markers onto one of the three datum planes of a Cartesian coordinate system.

In this case, the locus curve for each marker is recorded in three-dimensional space with temporal resolution and is stored as a data field of a data record which is common to all markers. The locus curves representing the movement pattern are then characterized by means of a data processing system using characteristic variables derived from the data record. Each characteristic variable is subsequently compared with reference variables derived accordingly from a stored reference data record, in the style of pattern recognition. To this end, the or each reference variable is ascertained, in a reference measurement, as a characteristic variable of a reference movement pattern. In this context, characteristic variable and reference variable are understood to mean any information which can be derived from the locus curves in order to characterize the movement pattern with regard to pattern recognition.

In this regard, the invention sets out from the consideration that more or less prediagnostic statements that can be derived from a cranio-corpo-gram are based on empirically obtained experimental values. Reliable diagnosis of a clinical picture on the basis of an observed movement pattern therefore requires a multiplicity of reference examinations, because individual properties that are also contained in the movement pattern need to be isolated from pathological properties. The amount of data needed to be processed for statistical validation of the findings becomes so complex that reliable statements are possible only when a lot of time is involved. However, time-consuming evaluation of an examination makes any use in the clinical field unprofitable. Furthermore, it is desirable to keep the loss of information when recording an experiment as low as possible, especially since new findings frequently necessitate renewed evaluation of old examinations or experiments from a new standpoint. Automatic pattern recognition using a computer or a data processing system can result in a particularly detailed analysis of a movement pattern, resulting in standardization of movement forms. It is acknowledged that this result can already contain a probability statement for later diagnosis.

As a result of the three-dimensional recording with temporal resolution, the data record contains all the information from the experiment. In particular, the locus curves for the markers can always be evaluated in isolation from one another. Furthermore, the time profile of the movement pattern is particularly easy to analyze. Modern data processing systems significantly reduce the time required for evaluation as compared with that for manual evaluation of the movement pattern.

The characteristic variables are derived from a projection of at least one locus curve onto one of the datum planes of a Cartesian coordinate system. In comparison with a method disclosed in WO 91/15148 for determining the movement of the cervical spine using three-dimensional representations that are ascertained from three-dimensional image information for a head movement, the locus curve can be displayed, e.g. on a screen, particularly clearly in a two-dimensional projection and can be evaluated efficiently. This is particularly advantageous since the evaluation result used for diagnostic or prediagnostic purposes should be comprehensible for each method step.

Typically, the movement pattern observed in a cranio-corpo-gram shows a periodic structure caused by any body sway in the subject. In a so-called stepping test (based on Unterberger/Fukuda), in which the subject makes stepping movements, half a sway cycle is equivalent to one step by the subject. To derive characteristic variables which give a particularly detailed description of the movement pattern, it is expedient to subdivide the locus curve into sequences on the basis of its periodicity. Particular characteristic variables are therefore ascertained from an individual sequence. Such characteristic variables are, by way of example, the amplitude, the sway duration and the distance covered transversely with respect to the direction of sway (step length).

Since it is acknowledged that the periodicity possessed by any body sway has no exact periodicity in the mathematical sense, the individual sequences are not identical, but only similar. Expediently, in addition or as an alternative to a characteristic variable ascertained from an individual sequence ("single-step" analysis), an appropriate characteristic variable is therefore ascertained from a number of sequences and is indicated statistically in the form of a mean with its standard deviation. This allows statements to be inferred about the regularity of any body sway.

Quantitative indications regarding the regularity of any body sway are expediently obtained by ascertaining the amplitude distribution and/or the frequency distribution of at least one locus curve. Thus, in particular, the frequency distribution is derived as a characteristic variable from the data record by means of a spectral analysis method, e.g. using so-called "Fast Fourier Transformation".

The movement of the body's center of gravity is ascertained in the form of further expedient characteristic variables. To this end, the distance between the starting position and the finishing position of the respective marker is calculated from the or from each data field of the data record. This can be used to determine the angle of deflection of the body, for example. In addition, characteristic variables ascertained using the mutually relative positions of the markers are used, where the characteristic variables represent the orientation of the body parts in space and their position, particularly that of the head and shoulders, relative to one another. These characteristic variables are, in particular, the intrinsic body spin and the torticollis angle, i.e. the movement of the head with respect to the shoulders. In addition, the length of the or of each locus curve, and hence the total distance covered by the respective marker, can be ascertained as a characteristic variable.

Using a pattern comparison of patterns derived from current data records and from stored reference data records, where the patterns are in the form of graphical elements, the particular degree of correspondence can be determined simply and effectively, using (neuro) fuzzy logic or a neural network. The appropriate graphical elements and/or other characteristic variables can be organized in terms of differential diagnosis. The reference data records are expediently supplemented by the particular current data record, in the manner of a self-learning knowledge base. In this instance, an identifier (associated with each reference data record) for a corresponding clinical picture or pattern allows the corresponding measurement to be evaluated for later diagnosis. Furthermore, an identifier additionally ascertained using the respective correspondence of the data record to a plurality of reference data records enables a probability statement regarding each of a plurality of prediagnosed clinical pictures to be made.

With the foregoing and other objects in view there is also provided, in accordance with the invention, an apparatus for performing the method. The apparatus includes the plurality of markers for attachment to a head and a trunk of the body of the subject during the configuration step. A data processing system is connected to a receiver configuration for recording the locus curve for each marker. The data processing system has a processing stage for calculating a data record that represents the locus curve from signals obtained from the receiver configuration. The receiver configuration can be a number of ultrasonic transceivers, CCD cameras (video cameras), photoelectric elements or the like, configured with a spatial distribution relative to one another, for recording and possibly preprocessing acoustic or optical signals. The corresponding receivers are expediently configured at right angles with respect to one another, so that the markers' locus curves are recorded in at least two different planes, e.g. the xy plane and the yz plane or xz plane. The coordinate data of the locus curve for the third plane can then be calculated from the measured data from the two receivers. When ultrasound is used instead of light for marking purposes, the measurement can also be carried out in an undarkened room.

A database configured downstream of the processing stage is used for storing reference data records which have preferably been ascertained in a multiplicity of reference measurements. An analysis module or analysis stage in the data processing system uses the currently recorded data record and the corresponding reference data record to ascertain a number of characteristic variables and reference variables. A comparison module or comparison stage ascertains the degree of correspondence between the data records on the basis of the characteristic and reference variables, using pattern recognition, for example. The data processing system subsequently associates with each data record an identifier based on a clinical picture, and uses the identifier to transfer the data record to the database for the purpose of expanding the appropriate reference data record.

The processing stage associates the locus curve for each marker with the data record, expediently as a data field. This produces a matrix containing a number of data fields which corresponds to the number of markers, each data field containing the three spatial coordinates based on a Cartesian coordinate system at the respective instant. The processing stage advantageously has a temporary data record store for temporarily storing the recorded measured data configured downstream of it.

The advantages obtained with the invention are, in particular, that computer-assisted evaluation of the measured data ascertained for a multiplicity of optically or acoustically recorded movement patterns, and the interpretation of curve profiles and function patterns derived therefrom using appropriate characteristic variables, enable a statement to be made about the clinical picture of a disorder forming the basis of the respective movement pattern. This statement can be used for diagnosis. While measured data is recorded on the subject's body virtually without contact, evaluation takes place in a data processing system which is detached from the subject's body and in which the measured data is processed and prepared for pattern recognition outside the body.

The evaluation of, in particular, typical clinical pictures showing head/body movement patterns for both ordinary subjects and striking subjects allows a knowledge base to be created containing a multiplicity of reference data and patterns. This knowledge base can be used to associate currently recorded and undiagnosed movement patterns with known clinical pictures. This allows qualitative and quantitative statements to be made, in particular, about psychological, psychosomatic, and/or neurological disorders, such as schizophrenia, depression, and Parkinson's syndrome, on the basis of the evaluation of the ascertained characteristic variables.

Other features which are considered as characteristic for the invention are set forth in the appended claims.

Although the invention is illustrated and described herein as embodied in a method and apparatus for evaluating a movement pattern, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
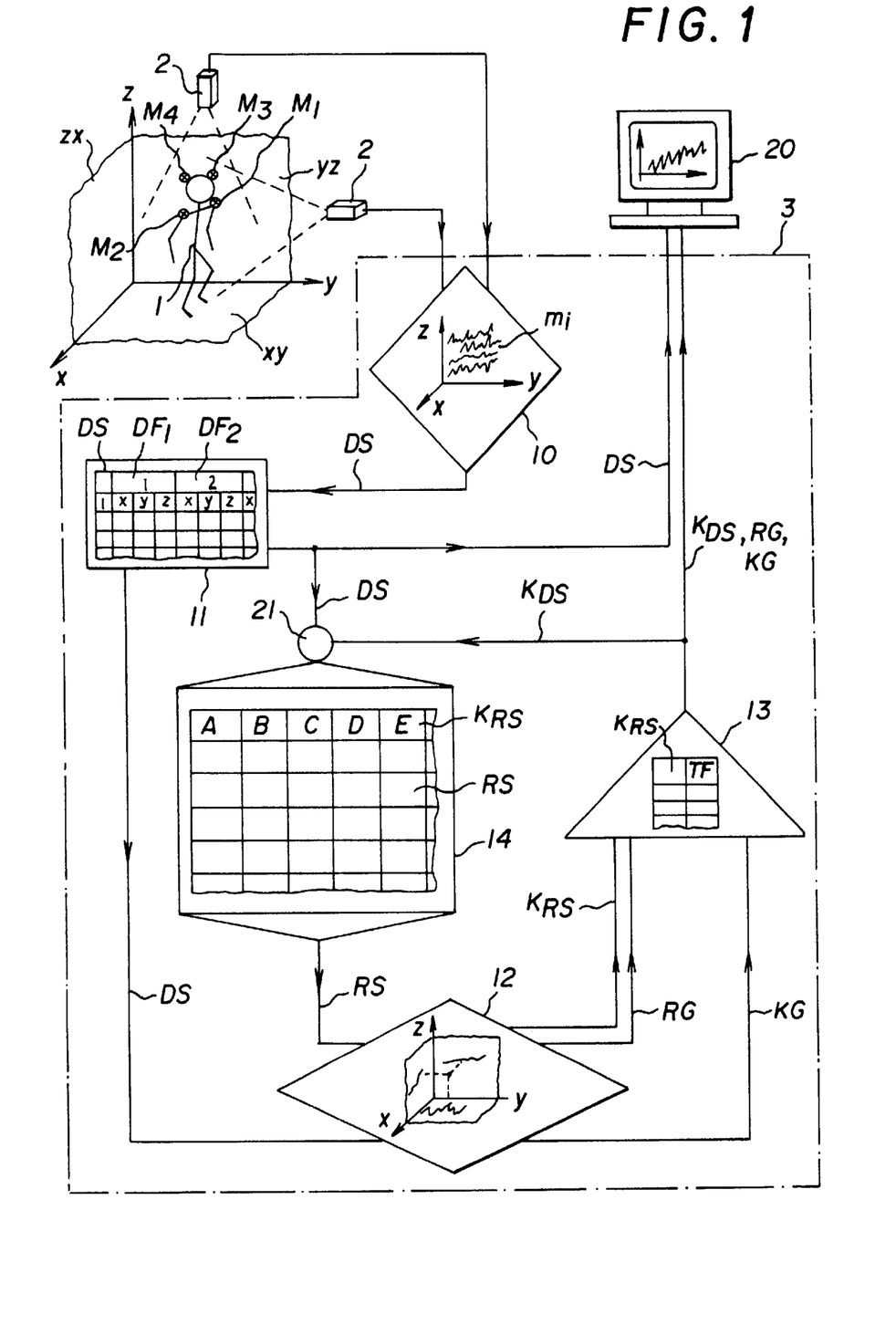
FIG. 1 is a schematic illustration of an apparatus having components provided for evaluating a movement pattern.

To record the movement pattern of a subject 1, two receivers 2 oriented at right angles to one another are provided, as shown in FIG. 1. These receivers 2 receive (not shown in more detail) signals from a number of markers $M_i$ (where, i=1–4 in the example shown) moving together with the subject 1. Movement of the body of the subject 1 can be visualized optically with particular ease. In this case, incandescent lamps or light-emitting diodes are used as the markers $M_i$, and, accordingly, a respective camera, such as a video camera, is used as a receiver 2. The movement pattern can also be marked using ultrasonic transmitters as the markers $M_i$ and ultrasonic receivers as the receivers 2. Alternatively, passive markers $M_i$ can also be used, which simply reflect the signal emitted by an external source. As is usual in so-called cranio-corpo-graphy, the observation is in this case expediently restricted to the head and trunk movement of the subject 1. For this purpose, a respective marker $M_1$ and $M_2$ is placed on the left and right shoulders of the subject 1, as well as a respective further marker $M_3$ and $M_4$ above his/her forehead and the back of his/her head.

The receivers 2 supply a respective two-dimensional image of the movement of the markers M to a processing stage 10 which is contained in a data processing system 3 and uses the images transmitted from the receivers 2 to establish the locus curve $m_i$ for each marker $M_i$ in three-dimensional space as a function of time t. The spatial coordinates of each locus curve $m_i$ are shown in a Cartesian coordinate system x,y,z, the starting position of the subject 1 being associated with the origin, and hence the x axis corresponding to the lateral axis. The y axis then runs horizontally in the walking direction of the subject 1, while the z axis extends vertically upward. The datum planes in the coordinate system, which are formed by the respective axes, are the xy plane (horizontal), the yz plane (longitudinally vertical) and the zx plane (laterally vertical).

The locus curve $m_i$ of each marker $M_i$ is calculated by means of the data processing system 3 using an algorithm in the processing stage 10. If an analog recording technique is used for the receivers 2, the processing stage 10 first converts analog data into digital data. The processing stage 10 transfers the locus curves $m_i$ as a data record DS to a preferably temporary data record store 11. In this case, the data record DS is divided into data fields $DF_i$, with a data field $DF_i$ representing the locus curve $m_i$ of a marker $M_i$. The data record store 11 makes the data record DS available to an analysis module 12 implemented in software form. The analysis module 12 first produces a respective projection of the locus curves $m_i$ onto the datum planes xy, yz and zx by selecting data from the data record DS. Since the locus curves $m_i$ typically have a periodic structure caused by body sway, an algorithm in the analysis module 12 additionally subdivides the locus curves $m_i$ into periodic sequences. Such a sequence, whose start and end are each characterized by a sharp change in direction of the locus curve $m_i$, then corresponds to exactly one cycle of the body sway. Further algorithms in the analysis module 12 additionally derive a number of characteristic variables KG from the locus curves $m_i$ which are projected onto the datum planes xy, yz and zx and are subdivided into sequences.

Characteristic variables KG are, in the first instance, derived by geometrical and physical measurement of the locus curves $m_i$. On the basis of the periodic structure of each locus curve $m_i$, relevant characteristic variables KG are, in particular, the amplitude, the period duration, the frequency of any sway and the distance covered transversely with respect to the direction of sway during a sway period (step length). These characteristic variables KG can either be ascertained from an individual sequence (single-step analysis) or can be derived statistically from a number of sequences and indicated in the form of a mean and a standard deviation (whole-reaction analysis). Furthermore, irregularities in the body sway are quantified by indicating an amplitude distribution and a frequency distribution obtained by means of spectral analysis (Fourier transformation). In addition, physical characteristic variables KG are ascertained from the movement of the body's center of gravity, the rotation of the body with reference to space and the rotation of the head relative to the trunk. For this purpose, the locus curves $m_i$ of a plurality of markers $M_i$ are combined with one another.

In addition to the physical and/or geometrical characterization, in the second instance, the analysis module 12 ascertains the correspondence of the line shape of the locus curves $m_i$ with comparison patterns stored as a graphical element. A comparison with a graphical element can also be based on an individual sequence or on the entire locus curve $m_i$. In this context, sway sequences are characterized using the shape of their reversal regions. Typical graphical elements have arcuate, looped or pointed reversal regions. By contrast, graphical elements for describing the entire locus curve $m_i$ are oriented using the contour of the area covered by a projection of a locus curve $m_i$. This contour is compared with graphical elements in the form of geometrical figures (e.g. triangle, square etc.) or comparatively complicated patterns (e.g. butterfly shape). The analysis module 12 transfers the characteristic variables KG derived from the data record DS to a comparison module 13.

To assess the data record DS, a reference data record RS is made available to the analysis module 12 from a database 14.

The reference data record RS has a data structure based on the data record DS, but is additionally provided with an identifier $K_{RS}$ based on a clinical picture. The analysis module 12 uses the reference data record RS to ascertain a number of reference variables RG, which are derived in an equivalent manner to the characteristic variables KG of the data record DS. Having been derived, the reference variables RG are likewise supplied to the comparison module 13. The reference data record RS is created in a reference measurement in a similar way to the creation of the data record DS. Together with the reference variables RG, the identifier $K_{RS}$ for the associated reference data record RS is transferred to the comparison module 13. In the comparison module 13, the characteristic variables KG and the reference variables RG are used to ascertain the degree of correspondence between the data record DS and the reference data record RS. As a result of particular graphical elements being associated with typical clinical pictures, a direct pattern comparison is used to standardize a current movement pattern directly, or at least to classify it qualitatively. Further characteristic variables KG are used to support the association in quantitative terms.

The pathological properties of the movement pattern of a subject 1 are always overlaid with individual properties. Furthermore, elements or symptoms—and hence individual characteristic variables KG—of the movement patterns for different clinical pictures can be the same or similar. In addition, an examination carried out on a subject 1 cannot be reproduced exactly. Both the characteristic variables KG and the reference variables RG are therefore generally nebulous in terms of their prediagnostic importance. To take this nebulosity into account, the comparison module 13 preferably operates on the basis of so-called fuzzy logic. According to the rules of fuzzy logic, a characteristic variable KG or reference variable RG input as an exact measured value is made nebulous (fuzzified) artificially. By comparing a nebulous characteristic variable KG with a nebulous reference variable RG, the comparison module 13 ascertains a standardization factor TF indicating the degree of correspondence. On account of the fuzzification, the standardization factor TF reflects the pathological correspondence between the data record DS and the reference data record RS to a greater extent. Individual, nonreproducible details in the movement pattern are filtered out by means of the fuzzy logic as a result of the nebulous manner of consideration. This is reflected in the indication of a probability of correspondence to the reference data record RS during subsequent defuzzification.

To ascertain an identifier $K_{DS}$ (based on a clinical picture) for the data record DS, the comparison module 13 carries out (as described) a comparison between the data record DS and a multiplicity of reference data records RS taken from the database 14. Finally, the standardization factors TF obtained for each individual comparison between a data record DS and a reference data record RS are overlaid and used for ascertaining the identifier $K_{DS}$. In this case, the identifier $K_{DS}$ is ascertained using a neural network, for example.

To output the identifier $K_{DS}$, the comparison module 13 is connected to an output module 20, e.g. a screen, a printer or a plotter. This output module 20 can also be used to output the movement pattern placed in the data record store 11 in the form of the data record DS. Finally, a database input controller 21 is used to provide the data record with the associated identifier $K_{DS}$, and the data record DS is added to the database 14 as a reference data record RS on the basis of this identifier $K_{DS}$, in the style of a self-learning knowledge base.

Figure 2:
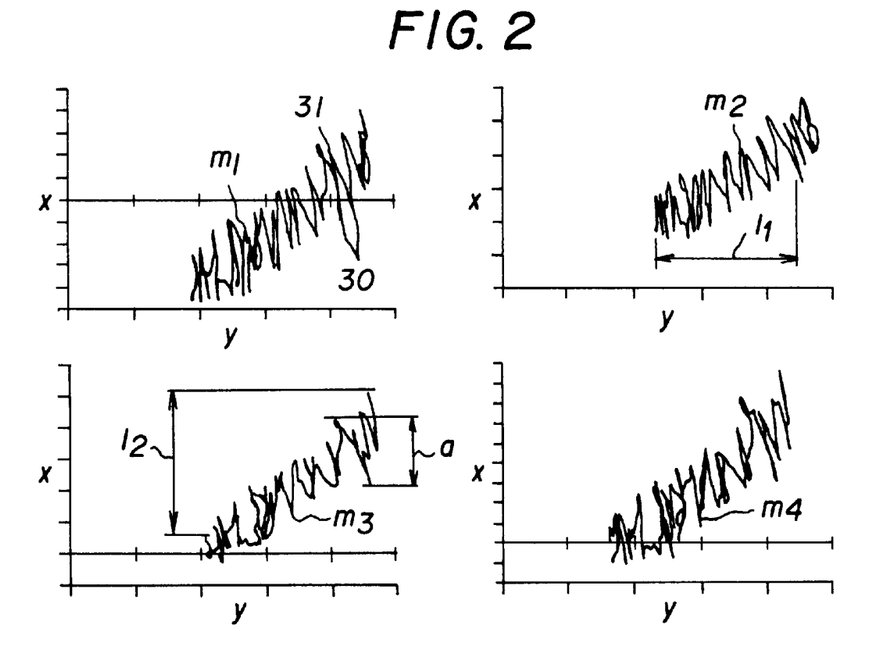
FIG. 2 shows a movement pattern that is produced for a series of steps by a subject and is represented by locus curves for four markers in a projection onto the xy plane.

FIG. 2 shows a movement pattern, typical for an Unterberger/Fukuda stepping test, using the locus curves $m_1$ to $m_4$ for the markers $M_1$ to $M_4$ in a projection onto the horizontal plane xy. In such a stepping test, the subject 1 makes a stepping movement on the spot. Usually, the subject 1 is blindfolded for this purpose, in order to prevent visual orientation in space. The locus curves $m_i$ show a distinct undulating periodicity caused by the body's shift in weight during stepping. A sequence 31 localized by two adjacent reversal points 30, as shown by way of example in FIG. 2 using the locus curve $m_1$, thus represents a stepping cycle of the subject 1 containing two successive steps.

Typically, an ordinary subject 1 also propagates by a distance $I_1$, in the direction of the longitudinal axis y in the stepping test. A lateral deviation $I_2$ in the body's center of gravity, or the amplitude a of the lateral sway, is classified as pathological if a (critical) threshold value is exceeded. A comparison of the locus curves $m_i$ shown in FIG. 2 with the aforementioned sequential graphical elements results in a high level of correspondence to a pointed comparison pattern.

Figure 3:
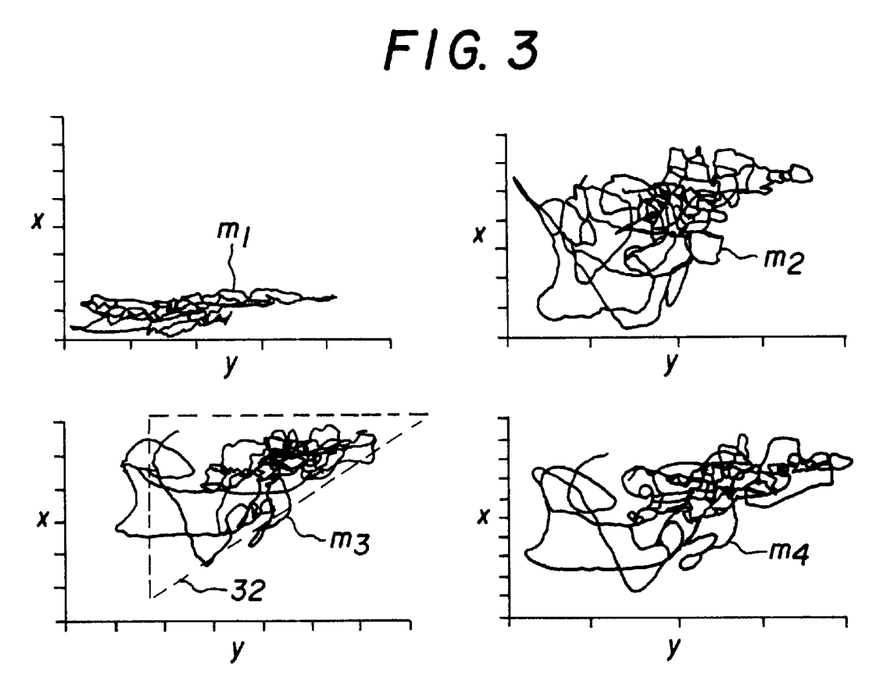
FIG. 3 is an illustration, based on FIG. 2, of a movement pattern produced when the subject is standing.

FIG. 3 shows a movement pattern for the same subject 1. However, this movement pattern was produced in a Romberg standing test. In this case, the subject 1 stands for approximately 1 minute, usually also blindfolded. The movement pattern produced during a standing test resembles a chaotically distorted circular movement with a smaller amplitude than in the stepping test (the scale of depiction used in FIG. 3 is about 10 times larger than the scale of depiction used in FIG. 2). The locus curve $m_i$ produced in a standing test, as shown in FIG. 3, is preferably wholly characterized using graphical elements. For these locus curves $m_i$, their contour is produced in line with a high level of correspondence to the right-angled triangle 32 which is also shown in FIG. 3 by way of example.

Figure 4A:
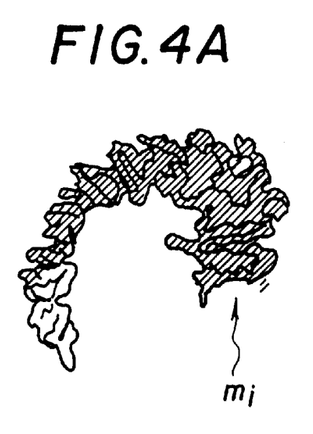
FIGS. 4A–4C show a movement pattern that has changed as a result of therapy.
Figure 4B:
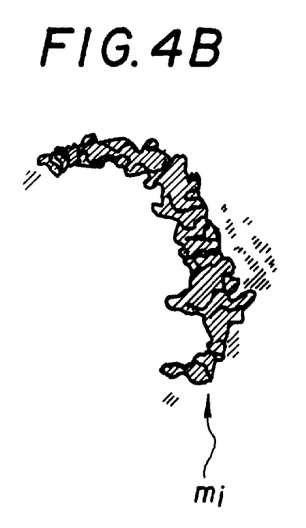
Figure 4C:
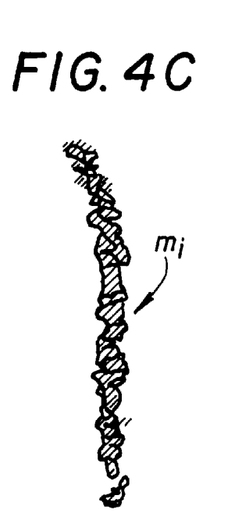

In addition to recognition of a clinical picture, the method can also be used as a method of examination accompanying therapy. FIG. 4 shows the recording of a stepping test carried out a plurality of times on a schizophrenic patient, the movement pattern shown in FIGS. 4a, 4b and 4c having been recorded at intervals of 30 days in each case. The success achieved with the treatment during therapy is shown in the leftward curvature of the locus curves $m_i$, which decreases progressively from FIG. 4a to FIG. 4c. The method is therefore particularly advantageously consulted as a measurement method for checking the medication stabilization of a patient.

We claim:

1. A method for evaluating a head and trunk movement pattern of a subject, which comprises:

configuring a plurality of markers to move together with the body of a subject;

for each of the plurality of markers, detecting a locus curve in three-dimensional space as a function of time and storing the locus curve as a data field of a measured data record that is common to the plurality of markers;

characterizing a movement pattern of the body of the subject using characteristic variables derived from the measured data record;

deriving reference variables from a stored plurality of reference data records;

comparing each of the characteristic variables with the reference variables derived from the stored reference data records;

deriving each of the characteristic variables from a projection of the locus curve of at least one of the plurality of markers onto one of the three datum planes of a Cartesian coordinate system; and ascertaining at least one characteristic variable representing a length of one of the locus curves.

2. The method according to claim 1, which comprises:

using the locus curve of at least one of the plurality of markers to ascertain a plurality of sequences corresponding to a sway cycle of body sway; and deriving at least one of the characteristic variables from a particular one of the sequences.

3. The method according to claim 2, which comprises deriving a mean and a standard deviation of the at least one characteristic variable from a plurality of the sequences.

4. The method according to claim 1, which comprises using a periodic nature of at least one of the locus curves to ascertain a characteristic variable representing a distribution of body sway, the distribution selected from the group consisting of a frequency distribution and an amplitude distribution.

5. The method according to claim 1, which comprises ascertaining a characteristic variable, representing a movement of the center of gravity of the body, from a distance between a starting position and a finishing position of at least one of the plurality of markers.

6. The method according to claim 1, which comprises ascertaining at least one characteristic variable, representing an orientation of a body part in space, using positions of the plurality of markers.

7. The method according to claim 1, which comprises ascertaining a characteristic variable, representing an attitude of a body part with respect to an attitude of another body part, from positions of the plurality of markers.

8. The method according to claim 1, which comprises ascertaining a characteristic variable representing a degree of correspondence between a pattern stored as a graphical element and a shape of at least one part of one of the locus curves.

9. The method according to claim 1, which comprises using fuzzy logic to ascertain at least one standardization factor indicating a degree of correspondence between the measured data record and at least one of the stored plurality of reference data records.

10. The method according to claim 1, which comprises:

storing the plurality of reference data records in a database;

associating a respective identifier based on a clinical picture with each of the plurality of reference data records; and using respective correspondences between the measured data record and the plurality of stored data records to ascertain an identifier for the measured data record.

11. The method according to claim 10, which comprises using a neural network to perform the step of ascertaining the identifier for the measured data record.

12. The method according to claim 10, which comprises obtaining a self-learning knowledge base by adding the measured data record to the database using the identifier of the measured data record.

13. An apparatus for performing the method according to claim 1, comprising:

the plurality of markers for attachment to a head and a trunk of the body of the subject during the configuration step; two receivers configured at right angles with respect to each other for detecting the locus curve for each of the plurality of markers, the receivers for providing signals; and a data processing system including:

a processing stage for calculating the measured data record representing the locus curve from the signals of the two receivers;

the database for storing the reference data record;

an analysis module for deriving the characteristic variables from the measured data record and for deriving the reference variables from the plurality of reference data records; and a comparison module comparing each of the characteristic variables with the reference variables to ascertain a degree of correspondence between the measured data record and at least one of the plurality of reference data records.

14. The apparatus according to claim 13, wherein the processing stage is configured to associate the locus curve for each of the plurality of markers with the data field of the measured data record.

15. The apparatus according to claim 13, wherein the processing stage includes a temporary data record storage device.

16. The apparatus according to claim 13, wherein the comparison module is configured to associate the measured data record with an identifier based on a clinical picture and to supply the data record to the database using the identifier.

17. The apparatus according to claim 13, wherein the data processing system is configured to supply the characteristic variables to an output module for displaying a movement pattern selected from the group consisting of a measured movement pattern and a reference movement pattern.

* * * * *